US005399797A

United States Patent [19]

Petrosky et al.

[11] Patent Number: 5,399,797

[45] Date of Patent: Mar. 21, 1995

[54] MANUFACTURE OF PERCHLOROETHYLENE BY CHLORINATING HYDROCARBONS AND PARTIALLY CHLORINATED HYDROCARBONS IN THE PRESENCE OF HYDROGEN

[75] Inventors: Jimmie T. Petrosky; Steven R. Hieger, both of Wichita; Evert E. Gannaway, Clearwater; Charles R. Cupit, Wichita, all of Kans.

[73] Assignee: Vulcan Materials Company, Wichita, Kans.

[21] Appl. No.: 199,696

[22] Filed: Feb. 22, 1994

Related U.S. Application Data

[63] Continuation of Ser. No. 16,236, Feb. 11, 1993, abandoned.

[51] Int. Cl.[6] .............................................. C07C 17/10

[52] U.S. Cl. .................................... 570/234; 570/218; 570/237

[58] Field of Search ........................ 570/234, 218, 237

[56] References Cited

U.S. PATENT DOCUMENTS

| | | |
|---|---|---|
| 2,442,324 | 5/1948 | Heitz et al. . |
| 2,857,438 | 10/1958 | Obrecht et al. . |
| 3,234,295 | 2/1966 | Sprauer . |

*Primary Examiner*—Howard T. Mars

*Attorney, Agent, or Firm*—Burns, Doane, Swecker & Mathis

[57] ABSTRACT

Perchloroethylene and hydrogen chloride are made by noncatalytic thermal chlorination of hydrocarbons and/or their partially chlorinated derivatives by reacting them with chlorine in the presence of hydrogen and carbon tetrachloride as a reactive diluent, under conditions which maximize consumption of carbon tetrachloride and minimize the production of heavy ends, such as hexachlorobenzene and other tarry products.

27 Claims, 2 Drawing Sheets

Hydrocarbon Feedstock
(4)
Products
Out (10)
Reactor (3)
Mixing
Nozzle (2)
Mixing Zone (1)
Reaction Zone (9)
Mixed Gases to Reactor
Hydrogen
(5)
Liquid Diluent
(6)
Vapor Diluent
(7)
Chlorine (8)

MANUFACTURE OF PERCHLOROETHYLENE BY CHLORINATING HYDROCARBONS AND PARTIALLY CHLORINATED HYDROCARBONS IN THE PRESENCE OF HYDROGEN

CROSS-REFERENCE TO RELATED APPLICATIONS

This application is a continuation of U.S. Ser. No. 08/016,236, filed Feb. 11, 1993, now abandoned, which application is incorporated herein by reference in its entirety.

BACKGROUND OF THE INVENTION

1. Field of the Invention

This invention relates to a process for making perchloroethylene and hydrogen chloride by noncatalytic thermal chlorination of hydrocarbons or their partially chlorinated derivatives in the presence of hydrogen and carbon tetrachloride. In particular, it relates to a process for production of perchloroethylene and hydrogen chloride by the noncatalytic thermal chlorination of $C_1$ to $C_3$ hydrocarbons and/or their partially chlorinated derivatives in the presence of hydrogen using carbon tetrachloride as a reactive diluent under conditions which maximize consumption of carbon tetrachloride supplied to the process from an external source, while minimizing the production of heavy ends, such as hexachlorobenzene and other tarry products.

2. Background of the Invention

When conventionally manufacturing perchloroethylene by chlorination of hydrocarbons and/or their partially chlorinated derivatives, substantial amounts of carbon tetrachloride are also obtained. In addition, substantial quantities of undesirable hexachlorinated products such as hexachloroethane, hexachlorobutadiene and hexachlorobenzene, hereinafter referred to as heavy ends, are formed. Carbon tetrachloride, however, is thought to be among the halocarbons which cause destruction of the ozone layer and is therefore coming to be considered a relatively undesirable by-product which is finding fewer and fewer commercial uses. More particularly, demand for it as a feedstock in producing fully halogenated chlorofluorocarbons, which previously provided an important market for carbon tetrachloride, has greatly decreased because of the environmentally deleterious nature of such chlorofluorocarbons. Because of the undesirable environmental attributes of carbon tetrachloride and products made therefrom, regulations governing the production and use of carbon tetrachloride are expected to result in a major decrease in the demand for carbon tetrachloride over the next decade. On the other hand, the more ecologically benign chlorinated hydrocarbons, notably perchloroethylene, are expected to remain in high demand because of their many practical uses, both as a solvent and as a starting material for the production of other chemicals. The present invention addresses this situation by providing a process for the production of perchloroethylene that consumes carbon tetrachloride and minimizes formation of heavy ends.

Direct thermal chlorination of methane, ethane, propane, ethylene, propylene, or their partially chlorinated derivatives exemplifies a conventional process for perchloroethylene production. The chemical reactions for the chlorination of these hydrocarbons and/or their partially chlorinated derivatives are exothermic. They can therefore result in carbon formation or result in an explosion from a runaway reaction if the temperature of the reaction is not controlled. One method of controlling the temperature in the reaction zone is to add a coolant or diluent to the feed mixture. A diluent is defined as any material that is injected into the reactor in order to moderate or control the reactor temperature. The use of vaporized carbon tetrachloride as a diluent to control reactor temperature is disclosed, for example in U.S. Pat. Nos. 2,577,388 and 2,442,323. These patents also disclose recycling of reaction products and use of other variables to control the ratio of carbon tetrachloride to perchloroethylene in the product stream. Use of a liquid diluent made up of chlorinated aliphatic compound such as carbon tetrachloride, perchloroethylene, hexachloroethane, hexachlorobutadiene, and mixtures thereof, is disclosed in U.S. Pat. No. 2,857,438.

It is also known to produce perchloroethylene by pyrolysis of carbon tetrachloride at high temperatures, as disclosed in U.S. Pat. No. 1,930,350. As disclosed in U.S. Pat. No. 3,364,272, the pyrolyric process for production of perchloroethylene ordinarily requires temperatures of the order of 800° C. The pyrolysis of carbon tetrachloride disclosed in U.S. Pat. No. 2,447,410 requires a temperature of 1300° C. to 1400° C. The production of perchloroethylene at these high temperatures, however, has serious disadvantages. Notably, the use of such high temperatures generally requires high energy input to initiate and maintain the reaction, expensive materials for reactor construction, and elaborate product separation to remove the unwanted heavy ends.

Catalytic systems have also been used to produce perchloroethylene. U.S. Pat. No. 4,002,695, for instance, discloses a process for preparing perchloroethylene by reaction of carbon tetrachloride vapor with hydrogen in the presence of a barium chloride catalyst at a temperature of at least 500° C. However, the catalysts required in this method are expensive and are subject to deactivation due to fouling with carbon. Coincidentally, the production of unwanted heavy ends, such as hexachloroethane, hexachlorobutadiene and hexachlorobenzene, is promoted by the use of such a catalyst.

SUMMARY OF THE INVENTION

Figure 1:
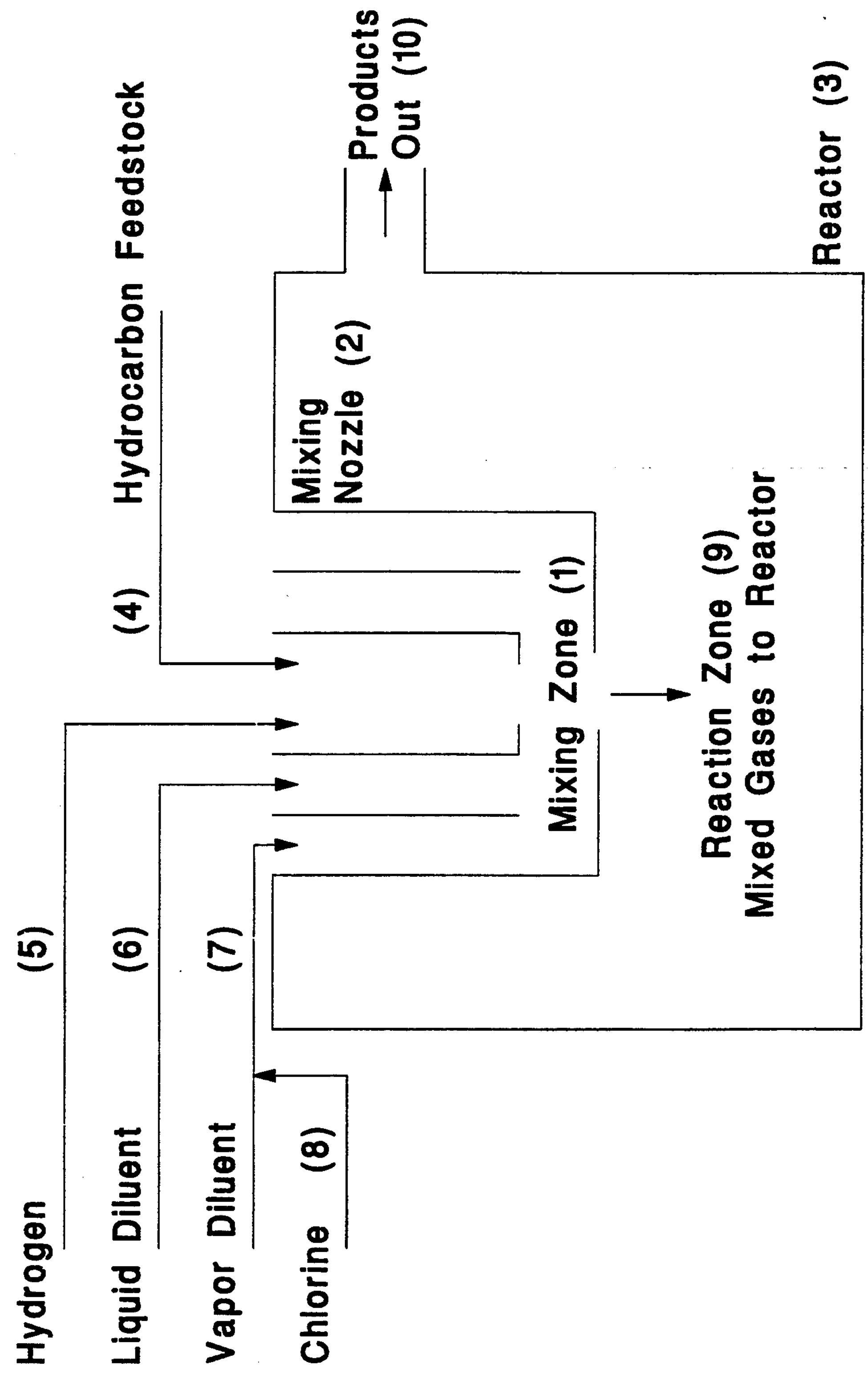
FIGS. 1 and 2 are schematic representations of two types of mixing schemes for introducing feed into the reaction zone. In these schemes, the feed is introduced into a mixing nozzle comprising a mixing zone where the reactants are premixed, the mixing nozzle is inserted through a feed port into the reaction zone of the reactor, and the feed comprising the pre-mixed reactants is discharged from the mixing nozzle into the reaction zone of the reactor.

The present invention provides a noncatalytic thermal process for making perchloroethylene by chlorination of a hydrocarbon feedstock, partially chlorinated hydrocarbon feedstock, or mixture thereof, comprising a compound having the formula $C_xH_yCl_z$, wherein x=1 to 3, y=1 to 8 and z—0 to 6 provided that y+z equals 2x+2 when the compound is saturated and equals 2x when the compound contains one double bond. The process is conducted by introducing the hydrocarbon feedstock, partially chlorinated hydrocarbon feedstock, or mixture thereof, elemental chlorine, elemental hydrogen, and carbon tetrachloride into a reaction zone maintained at a temperature in the range between about 500° and about 700° C., wherein consumption of unwanted carbon tetrachloride is maximized and product selectivity is improved while, unexpectedly, the production of heavy ends is minimized.

The chlorine is introduced into the reaction zone either as elemental chlorine or from the pyrolysis reaction of carbon tetrachloride. The chlorine is introduced in an amount sufficient to react with the hydrocarbon feedstock and hydrogen and result in unreacted chlorine in the reactor effluent, preferably in an amount sufficient to result in between about 3.5 and about 10.0 volume percent free, i.e., unreacted, chlorine in the reactor effluent or product mixture, which is commonly described as excess chlorine. The reaction of the chlorine with the hydrocarbon feedstock generates a portion of the heat required for the pyrolysis of carbon tetrachloride.

The hydrogen is introduced in an amount sufficient to react with a portion of the chlorine, which is either introduced into the reaction zone as elemental chlorine or is produced from the reaction of two carbon tetrachloride molecules. The hydrogen reacts with the chlorine in order to provide additional heat for the pyrolysis of carbon tetrachloride. The hydrogen is introduced in an amount in the range of from about 0.02 to about 1.0 mole hydrogen per mole of elemental chlorine introduced.

Carbon tetrachloride is introduced to serve both as a diluent and as a reactant in the reaction zone and is introduced in an amount sufficient to maintain the reaction temperature between about 500° and about 700° C., e.g., 1.0 to 100.0 moles carbon tetrachloride per mole of hydrocarbon feedstock. The carbon tetrachloride can be either in the vapor phase or liquid phase or a mixture of vapor and liquid phases, as is further disclosed in copending application U.S. Ser. No. (08/252,400) filed simultaneously herewith.

A gaseous product mixture containing carbon tetrachloride, chlorine, perchloroethylene and hydrogen chloride is withdrawn from the reaction zone and is condensed, whereupon perchloroethylene, hydrogen chloride and heavy ends are separated from the mixture. The process is characterized by a net consumption of carbon tetrachloride and minimization of the formation of heavy ends, such as hexachloroethane, hexachlorobutadiene and hexachlorobenzene.

DESCRIPTION OF THE PREFERRED EMBODIMENTS OF THE INVENTION

The pyrolysis of carbon tetrachloride to form perchloroethylene is represented by the following equation:

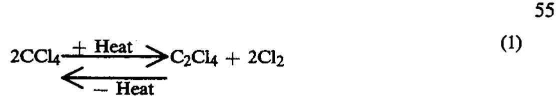

$$2CCl_4 \underset{-\text{ Heat}}{\overset{+\text{ Heat}}{\rightleftharpoons}} C_2Cl_4 + 2Cl_2 \quad (1)$$

The reaction is an equilibrium reaction that is endothermic and favors the formation of carbon tetrachloride under conventional conditions. The promotion of the formation of perchloroethylene, a commercially important product, accompanied by maximum consumption of unwanted carbon tetrachloride is increasingly recognized as being desirable.

It has been found that the addition of elemental hydrogen and excess chlorine to the reactor can result in an increase in the amount of carbon tetrachloride consumed during production of perchloroethylene by chlorination of a hydrocarbon feedstock while at the same time providing the heat required for the pyrolysis of the carbon tetrachloride. The elemental hydrogen reacts with a portion of the chlorine in the reactor, as shown in equation (2):

$$(2)\ H_2+Cl_2 \rightarrow 2\ HCl+\text{Heat}$$

This reaction generates heat in the reactor chamber and thus helps to drive forward the endothermic reaction of equation (1), which results in the production of perchloroethylene and consumption of carbon tetrachloride.

It has further been found, however, that this release of heat and the concurrent chlorination of the hydrocarbon feedstock requires careful control and that this control can be achieved by having a suitable proportion of carbon tetrachloride in the reactor, where it acts not only as a diluent but also as an additional source for producing perchloroethylene. The result is that under fixed reaction zone conditions of temperature and pressure, and in the presence of hydrogen and excess chlorine, the hydrocarbon feedstock is chlorinated to produce principally perchloroethylene and carbon tetrachloride while the carbon tetrachloride formed in the reaction as well as the carbon tetrachloride introduced are pyrolyzed, resulting in a net consumption of carbon tetrachloride. The conversion of carbon tetrachloride to perchloroethylene is as shown by equation (1).

By combining reactions (1) and (2), the overall net reaction shown below results:

$$(3)\ 2CCl_4+2H_2 \rightarrow C_2Cl_4+4HCl$$

In addition to consuming carbon tetrachloride, reaction (3) produces perchloroethylene without any substantial or significant conversion of valuable reactants to undesirable heavy ends, such as hexachloroethane, hexachlorobutadiene and hexachlorobenzene. This avoids or minimizes environmental difficulties and expense normally associated with the disposal of such heavy ends.

The "hydrocarbon feedstock," as this term is used in this specification, may be, for instance, methane, ethane, propane, ethylene, propylene, and their partially chlorinated derivatives, such as chloroform, methyl chloride, ethyl chloride, ethylene dichloride, trichloroethane, trichloropropane, and the like. With respect to methane, ethane and propane the results of total chlorination of the hydrocarbon are represented by the following equations:

$$(4)\ CH_4+3\ Cl_2 \rightarrow 0.5\ C_2Cl_4+4\ HCl$$

$$(5)\ CH_4+4\ Cl_2 \rightarrow CCl_4+4\ HCl$$

$$(6)\ C_2H_6+5\ Cl_2 \rightarrow C_2Cl_4+6\ HCl$$

$$(7)\ C_2H_6+7\ Cl_2 \rightarrow 2\ CCl_4+6\ HCl$$

$$(8)\ C_3H_8+7\ Cl_2 \rightarrow 1.5\ C_2Cl_4+8\ HCl$$

$$(9)\ C_3H_8+10\ Cl_2 \rightarrow 3\ CCl_4+8\ HCl$$

Similar equations can be given for the total chlorination of the partially chlorinated derivatives of the hydrocarbons.

As stated earlier herein, hydrogen and excess chlorine are introduced into the reaction zone in amounts sufficient to provide heat for the pyrolysis of carbon tetrachloride. The hydrogen is introduced at an addition rate preferably between about 0.1 and about 0.95 mole hydrogen per mole of hydrogen plus hydrocarbon feedstock. The specific addition rate depends upon the content of the hydrocarbon feedstock, for example, whether the hydrocarbon is saturated, unsaturated or partially chlorinated. Higher feed rates may be used and the consumption of carbon tetrachloride increases as the hydrogen feed rate increases. The chlorine is introduced such that between about 3.0% and about 10%, preferably between about 5.0% and about 7.0%, by volume unreacted chlorine is present in the reactor effluent or product mixture, which is commonly described as excess chlorine. Excess chlorine is required to ensure that no unreacted hydrogen is in the reactor effluent or product mixture. However, excess chlorine in amounts greater than the above described range will increase the carbon tetrachloride produced. Additional benefits of excess chlorine being introduced into the reaction zone, as stated in U.S. Pat. Nos. 2,442,324 and 2,727,076, include a reduction in the formation of heavy ends and the total chlorination of the hydrocarbon feedstock. Thus, by operating the reactor with an excess of chlorine in the reaction zone, the need to separate undesirable underchlorinated compounds in the purification step is eliminated.

The carbon tetrachloride is introduced into the reaction zone to serve as a diluent in an amount sufficient to maintain the temperature between about 500° and about 700° C., preferably between about 575° and about 625° C. Temperatures below about 500° C. result in incomplete reaction of the hydrocarbon feedstock, lower conversions of carbon tetrachloride to perchloroethylene, and formation of partially chlorinated compounds, such as chloroform or trichloroethylene. Higher temperatures, above about 700° C., result in carbon formation. The ratio of carbon tetrachloride to hydrocarbon feedstock introduced into the reaction zone will depend upon the particular hydrocarbon feedstock, the amounts of hydrogen and chlorine introduced, and the reactor conditions. If desired, inert diluents such as hydrogen chloride and/or nitrogen may be used to help control reactor temperatures. However, it is preferred to recycle liquid and vapor carbon tetrachloride and perchloroethylene mixtures from the process separation and/or distillation steps as well as introduce extraneous carbon tetrachloride diluent in order to control reactor temperatures. The carbon tetrachloride is recycled and converted to perchloroethylene, resulting in carbon tetrachloride consumption. Perchloroethylene is recycled if distillation results in incomplete separation of perchloroethylene and carbon tetrachloride.

The carbon tetrachloride may be introduced into the reaction zone either as a pure compound or as part of a mixed stream containing other chlorinated hydrocarbons, such as chloroform, perchloroethylene, trichloroethylene, hexachlorobutadiene, hexachlorobenzene or hexachloroethane. However, it is preferred to use a chloro-organic stream which has a carbon tetrachloride concentration of at least 50 weight percent.

Figure 2:
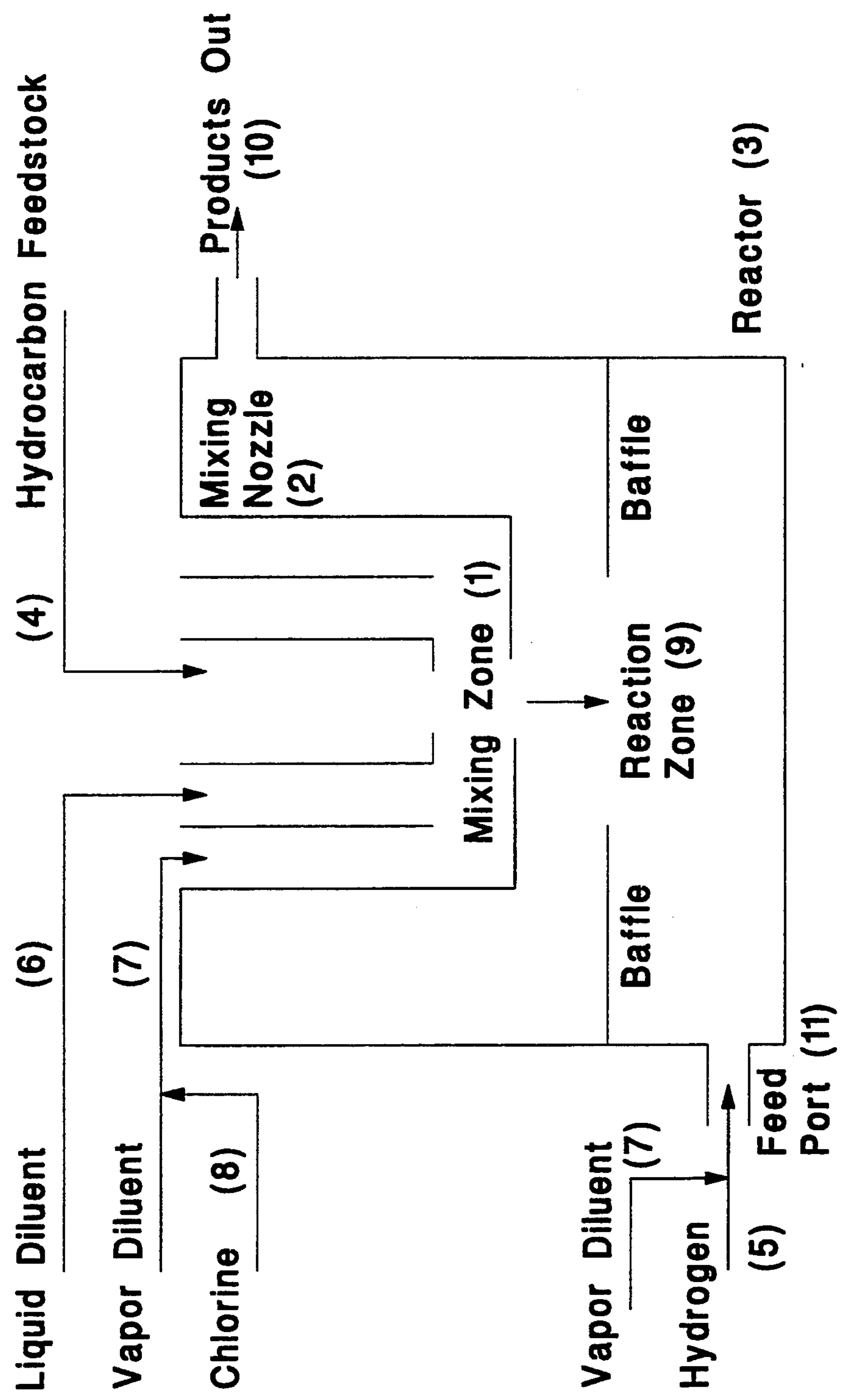

The reactants comprising the hydrocarbon feedstock, carbon tetrachloride diluent, chlorine and hydrogen can be injected directly into the reaction zone without a mixing nozzle if all the reactants and diluent are in the vapor phase as is common in the prior art. However, if the carbon tetrachloride is at least partially in the liquid phase, the hydrocarbon feedstock, carbon tetrachloride, chlorine and hydrogen are first introduced into an inlet of a mixing nozzle which is inserted or discharges into the reaction zone to achieve pre-mixing of the feed material. This practice improves the mixing efficiency of the reactants and thus increases the ability of the reaction zone to produce the desired products. Two types of mixing arrangements for introducing feed into the reaction zone through a mixing nozzle are schematically represented in FIGS. 1 and 2. The diagrams are meant only to be illustrative of the concept and should not be construed as all inclusive, thus limiting the invention.

As shown in FIG. 1, the preferred method of feeding, the hydrocarbon feedstock (4), hydrogen (5), liquid carbon tetrachloride (6), vapor carbon tetrachloride (7) and chlorine (8) can be introduced into the mixing zone (1) of the mixing nozzle (2) inserted into the reactor (3) to pre-mix the reactants. The reactor feed material enters the mixing zone (1) and is inserted or discharges into the reaction zone (9) of the reactor (3). The products of the reaction are then discharged from the reactor (10).

As shown in FIG. 2, the hydrogen with at least a portion of the vapor carbon tetrachloride diluent can be fed into the reactor in a feed port (11) separate from the mixing nozzle through which the hydrocarbon feedstock, chlorine, and remaining liquid and/or vapor carbon tetrachloride diluent are fed. In this method of feeding the reactants to the reaction zone of the reactor, the hydrogen and at least a portion of the vapor carbon tetrachloride are fed together to avoid carbon formation from "hot spots," i.e., localized zones of high temperature in the reactor due to rapid reaction with insufficient cooling or mixing. This method requires a 3 to 1 carbon tetrachloride to hydrogen mole ratio, thus limiting the amount of hydrogen that can be fed to the reactor. Similarly, the chlorine could be fed separately, however, no advantages are achieved by this method.

While the process of the present invention has been described as being conducted in one reactor, the present invention alternatively can be carded out in two separate reactor stages operating in series. The first stage consists of reacting the hydrocarbon feedstock with chlorine in the presence of carbon tetrachloride diluent. The reactor effluent is fed to a second stage reactor wherein the hydrogen and additional chlorine and/or carbon tetrachloride diluent are injected.

Various factors are important in controlling the degree of mixing of the liquid diluent with the other reactants and diluent that are supplied in the vapor phase reactor. These factors include the manner in which the liquid is introduced into the reaction zone of the reactor, the temperature and pressure of the liquid feed that is injected, the identity or composition of the liquid feed, the velocities of the materials to be mixed, and the conditions inside the reaction zone itself. In a preferred embodiment, the vapor feeds are introduced into the reaction zone of the reactor with a velocity through the orifice in the nozzle of at least about 30 meters per second (100 feet per second) and preferably between about 60 and about 77 meters per second (200 and 250 feet per second). The upper limit on the-velocity is sonic velocity, although such high velocity is not preferred. Although not essential to the invention, it may be desirable to heat the liquid and/or vapor feeds prior to injecting them into the reactor in order to increase the turbulence in the mixing zone of the mixing nozzle. Heating the vapor feeds to a higher temperature increases the volumetric flow of the gas which increases the velocity at which the vapor feed is introduced into the reaction zone and results in better mixing of the gases. Heating the liquid feed to a higher temperature increases its viscosity, which makes the liquid easier to atomize and results in better dispersion of the liquid in the vapor feed. One skilled in the art of nozzle design will recognize that additional methods may be useful in obtaining a high degree of turbulence in the mixing zone to promote good mixing prior to entering the reaction zone.

Reactor pressure is important, but not critical. While the preferred operating pressure is between about 0 and about 4.5 atmospheres gauge (50 psig), higher pressures can be employed e.g., between about 0 and about 10 atmospheres gauge. The reactor can either be a back-mixed or plug flow type with suitable refractory lining as is common in the industry.

The perchloroethylene product may be purified by conventional methods illustrated in the prior art, such as effluent quenching, condensing, and distillation in order to separate the perchloroethylene product from the unconverted carbon tetrachloride, hydrogen chloride, chlorine and other by-products.

The invention may be understood in more detail from the following illustrative examples. It should be understood that these examples are not construed as limiting the invention.

TABLE I

| Test No. | 1 | 2 | 3 | 4 | 5 | 6 |
|---|---|---|---|---|---|---|
| Feeds, kg/hr | | | | | | |
| $Cl_2$ | 21.9 | 24.0 | 23.8 | 23.9 | 24.3 | 21.6 |
| EDC | 8.4 | 9.0 | 9.1 | 9.1 | 8.9 | 6.0 |
| Hydrogen | — | .04 | .04 | .06 | .06 | .23 |
| Liquid $CCl_4$ | 5.7 | 8.1 | 9.4 | 5.6 | 5.9 | 7.3 |
| Vapor $CCl_4$ | 8.4 | 9.6 | 8.5 | 16.8 | 16.8 | 40.8 |
| Total | 44.4 | 50.7 | 50.8 | 55.5 | 56.0 | 75.9 |
| Excess $Cl_2$, vol. % (in reactor effluent) | 5.4 | 5.1 | 6.0 | 4.4 | 7.0 | 3.9 |
| Molar Ratio of $H_2$ to $Cl_2$ Introduced | — | .06 | .06 | .09 | .09 | .37 |
| Products, kg/hr | | | | | | |
| $CCl_4$ | 1.7 | — | — | — | — | — |
| $C_2Cl_4$ | 10.6 | 11.8 | 12.8 | 14.7 | 14.9 | 11.2 |
| $C_4Cl_6$ | .64 | .74 | .69 | .93 | .75 | .45 |
| $C_6Cl_6$ | .02 | .10 | .11 | .13 | .06 | .06 |
| HCl | 12.4 | 14.6 | 15.0 | 15.5 | 15.2 | 17.1 |
| $CCl_4$ Consumed, (kg/hr) | — | .6 | 1.5 | 3.5 | 4.6 | 4.9 |
| Molar Addition Rate of Reactants $H_2/(H_2 + EDC)$ | 0.0 | .169 | .188 | .242 | .245 | .658 |
| [1]Wt. Ratio of $CCl_4$ Consumed to $C_2Cl_4$ Produced $CCl_4/C_2Cl_4$ | −.16 | .05 | .12 | .24 | .31 | .43 |
| Wt. Ratio of Products Heavy Ends/$C_2Cl_4$ | .062 | .072 | .063 | .072 | .054 | .046 |

[1]Negative number indicates $CCl_4$ is produced

EXAMPLE 1

Liquid 1,2-dichloroethane (EDC), vaporized chlorine, elemental hydrogen, and a mixture of vapor and liquid diluent carbon tetrachloride were continuously introduced into a back-mixed reactor chamber. The reactor chamber consisted of a carbon lined vessel consisting of about 1.9 cubic feet of volume. The reaction chamber was maintained at a temperature of approximately 595° C. and at a pressure of 3.7 atmospheres gauge (40 psig). The hot reaction gases at the exit of the reactor were indirectly cooled with water in a quench tower with a bottoms temperature of about 165 ° C. The vapors of carbon tetrachloride and perchloroethylene going overhead of the quench tower were condensed by indirect cooling to separate them from the hydrogen chloride and unreacted chlorine, and fractionally distilled to recover the product and carbon tetrachloride. Some or all of the carbon tetrachloride diluent was fed as liquid and some or all of the carbon tetrachloride diluent was vaporized in a heat exchanger.

The effect of varying the amount of elemental hydrogen on chlorination of EDC, conversion of carbon tetrachloride to perchloroethylene, and heavy ends production are shown in Table I. As the amount of hydrogen is increased in tests from one (1) to six (6), the amount of carbon tetrachloride consumed increases. In run 1, the $CCl_4$ produced per unit weight of $C_2Cl_4$ is 0.16 kg/kg (note that negative number indicates $CCl_4$ is produced rather than consumed). However, as hydrogen feed to the reactor is increased, the consumption of carbon tetrachloride increases to 0.43 kg/kg of perchloroethylene produced (at a hydrogen feed rate of 0.658 mol per mol of $H_2$ plus EDC). Also as seen in Table I, the ratio of heavy ends produced is minimized by the addition of hydrogen. The heavy ends to perchloroethylene weight ratio decreased from 0.062 kg/kg (no hydrogen addition) to 0.046 kg/kg at the 0.658 mol/mol addition rate (mols $H_2$/(mols $H_2$+mols EDC)).

EXAMPLE 2

Example 1 is repeated with the exception that propane is used as the primary carbon-containing feed instead of EDC. The effect of varying the hydrogen addition rate on chlorination of propane, conversion of carbon tetrachloride to perchloroethylene, and heavy ends formation is shown in Table II. The consumption of carbon tetrachloride is maximized and the formation of heavy ends is minimized by the addition of hydrogen. At a hydrogen addition rate of 0.929 mol/mol ($H_2/H_2+C_3H_8$)), the consumption of $CCl_4$ was 1.04 kg/kg of perchloroethylene produced (test 13). When hydrogen was not added, as in test 10, carbon tetrachloride consumption was only 0.34 kg/kg of perchloroethylene produced. In addition, when hydrogen was added the heavy ends to perchloroethylene weight ratio decreased from 0.06 (no hydrogen addition) to 0.019 at the 0.929 molar addition rate of hydrogen (test 10 and test 13).

TABLE II

| Test No. | 10 | 11 | 12 | 13 |
|---|---|---|---|---|
| Feeds, kg/hr | | | | |
| $Cl_2$ | 22.7 | 26.3 | 22.7 | 18.6 |
| Propane | 1.8 | 1.6 | 1.0 | .50 |
| Hydrogen | — | .16 | .27 | .30 |
| Liquid $CCl_4$ | 11.4 | 23.1 | 27.2 | 22.2 |
| Vapor $CCl_4$ | 29.5 | 40.1 | 40.1 | 40.1 |
| Total | 65.4 | 92.0 | 92.0 | 87.0 |
| Excess $Cl_2$, vol. % (in reactor effluent) | 6.9 | 5.4 | 5.3 | 6.9 |
| Molar Ratio of $H_2$ to $Cl_2$ Introduced | — | .21 | .42 | .57 |
| Products, lb/hr | | | | |
| $C_2Cl_4$ | 11.09 | 11.09 | 9.30 | 9.64 |
| $C_4Cl_6$ | .22 | .27 | .23 | .11 |
| $C_6Cl_6$ | .44 | .58 | .13 | .08 |
| $CCl_4$ Consumed, (kg/hr) | 3.77 | 5.77 | 7.90 | 10.0 |
| Molar Addition Rate of Reactants $H_2/(H_2 + C_3H_8)$ | 0.0 | .686 | .929 | .929 |
| Wt Ratio of $CCl_4$ Consumed | .34 | .52 | .85 | 1.04 |

TABLE II-continued

| Test No. | 10 | 11 | 12 | 13 |
|---|---|---|---|---|
| to $C_2Cl_4$ Produced | | | | |
| $CCl_4/C_2Cl_4$ | | | | |
| Wt. Ratio of Products | .06 | .077 | .039 | .019 |
| Heavy Ends/$C_2Cl_4$ | | | | |

As can be seen from the examples, the chlorination of hydrocarbon feedstock to produce perchloroethylene and consume carbon tetrachloride is maximized by the introduction of elemental hydrogen and an excess of chlorine into the reaction zone, while minimizing the production of unwanted heavy ends. The consumption of carbon tetrachloride increases as the molar addition rate of hydrogen increases. The hydrogen is preferably introduced into the reaction zone at a molar addition rate of between about 0.1 and about 1.0 mole hydrogen per mole hydrogen plus hydrocarbon feedstock.

With the present teaching in hand, persons skilled in the art will be able to determine the optimum molar addition rate of hydrogen by performing routine preliminary tests for each case. The particular rate, however, will depend upon, for example, the particular hydrocarbon feedstock, the reactor conditions, the amount of chlorine introduced and whether the carbon tetrachloride diluent is in the vapor or liquid phase, or is a mixture of the vapor and liquid phases.

While the invention has been described in terms of certain preferred embodiments, modifications obvious to one with ordinary skill in the art may be made without departing from the scope of the present invention.

What is claimed is:

1. A noncatalytic thermal process for making perchloroethylene by chlorination of a hydrocarbon feedstock, partially chlorinated hydrocarbon feedstock, or mixture thereof, under conditions which maximize consumption of carbon tetrachloride, which process comprises introducing the following materials into a mixing zone:

(a) said feedstock having the formula $C_xH_yCl_z$, wherein x=1 to 3, y=1 to 8 and z=0 to 6, provided that y+z equals 2x+2 when the compound is saturated and equals 2x when the compound contains one double bond;

(b) chlorine and elemental hydrogen, the chlorine being introduced in an amount sufficient to convert said feedstock to perchloroethylene and leave unreacted chlorine in the resulting converted reaction mixture; and (c) carbon tetrachloride as a reactive diluent in an amount sufficient to maintain the reaction temperature between about 500° and about 700° C.;

discharging the resulting mixture from said mixing zone into a reaction zone wherein the temperature of the mixture is maintained within said temperature range and wherein carbon tetrachloride is consumed and perchloroethylene is produced; and withdrawing a product mixture which comprises perchloroethylene from the reaction zone, condensing the product mixture, and separating perchloroethylene from the product mixture.

2. The process of claim 1, wherein said feedstock is selected from the group consisting of ethylene dichloride and propane.

3. The process of claim 2, wherein the feedstock is propane, the hydrogen addition rate is between about 0.5 and about 0.9 mole per mole hydrogen plus propane, the chlorine is introduced in an amount sufficient to leave between about 5.0 and about 7.0 volume percent of free chlorine in the resulting converted reaction mixture, the reaction temperature is between about 575° and about 625° C., and the pressure in the reaction zone is between about 0 and about 10 atmospheres gauge.

4. The process of claim 1, wherein the carbon tetrachloride is introduced in the liquid phase.

5. The process of claim 1, wherein the carbon tetrachloride is introduced in the vapor phase.

6. The process of claim 1, wherein the carbon tetrachloride is introduced as a mixture of liquid and vapor.

7. The process of claim 1, wherein carbon tetrachloride separated from the product mixture is recycled to the reaction zone.

8. The process of claim 1, wherein carbon tetrachloride is introduced into the reaction zone from an extraneous source.

9. The process of claim 1, wherein the resulting mixture is introduced into the reaction zone from the mixing zone with a velocity of at least about 30 meters per second.

10. The process of claim 10, wherein the resulting mixture is introduced into the reaction zone from the mixing zone with a velocity of between about 60 and about 77 meters per second.

11. The process of claim 1, wherein a high degree of turbulence in the mixing zone is provided by preheating the reactants in the mixing zone.

12. The process of claim 5, wherein the elemental hydrogen is fed with a portion of the vaporized carbon tetrachloride into the reaction zone through a feed port separate from the mixing nozzle through which said feedstock, chlorine and remaining carbon tetrachloride are fed.

13. The process of claim 1, wherein said addition rate is between 0.1 and 1.0 mole per mole hydrogen plus said feedstock.

14. The process of claim 13, wherein the ratio by weight of carbon tetrachloride consumed to perchloroethylene produced is between 0.01 and 1.9.

15. The process of claim 14, wherein the ratio by weight of carbon tetrachloride consumed to perchloroethylene produced is between 0.05 and 1.25.

16. The process of claim 1, wherein the chlorine is introduced in an amount sufficient to leave between about 0.1 volume percent and about 15.0 volume percent of free chlorine in the resulting product mixture.

17. The process of claim 16, wherein the chlorine is introduced in an amount sufficient to leave between about 3.5 volume percent and about 7.0 volume percent of free chlorine in the resulting product mixture.

18. The process of claim 17, wherein the reaction temperature is between 575° and 625° C.

19. The process of claim 18, wherein the pressure in the reaction zone is between about 0 and about 4.5 atmospheres gauge.

20. The process of claim 19, wherein the reaction zone is in a back-mixed reactor or a plug flow type.

21. A noncatalytic thermal process for making perchloroethylene by chlorination of ethylene dichloride under conditions which maximize consumption of carbon tetrachloride, which process comprises introducing the following materials into a mixing zone:

(a) ethylene dichloride;

(b) chlorine and elemental hydrogen, the chlorine being introduced in an amount sufficient to convert ethylene dichloride to perchloroethylene and to leave unreacted chlorine in the resulting converted product mixture; and (c) carbon tetrachloride as a reactive diluent in an amount sufficient to maintain the reaction temperature between about 575° and about 625° C.;

discharging the resulting mixture from said mixing zone into a reaction zone wherein the temperature of the mixture is maintained within said temperature range and wherein carbon tetrachloride is consumed and perchloroethylene is produced; and withdrawing a product mixture which comprises perchloroethylene from the reaction zone, condensing the product mixture, and separating perchloroethylene from the product mixture.

22. The process of claim 21, wherein the hydrogen is introduced at an addition rate between about 0.1 and about 0.9 moles hydrogen per mole hydrogen plus ethylene dichloride.

23. The process of claim 21, wherein the diluent comprising carbon tetrachloride is a mixture of liquid and vapor phase carbon tetrachloride.

24. The process of claim 22, wherein any carbon tetrachloride separated from the product mixture is recycled to the reaction zone.

25. The process of claim 22, wherein the chlorine is introduced in an amount sufficient to leave between about 6.0 and about 7.0 volume percent of free chlorine in the resulting product mixture.

26. The process of claim 23, wherein the ethylene dichloride, elemental hydrogen, chlorine, and carbon tetrachloride are introduced into the reaction zone by means of a mixing nozzle.

27. The process of claim 23, wherein the elemental hydrogen is fed with a portion of the vaporized carbon tetrachloride into the reaction zone through a feed port separate from the mixing nozzle through which the ethylene dichloride, chlorine and remaining carbon tetrachloride are fed.

* * * * *